United States Patent [19]

Ochiai

[11] 4,158,198

[45] Jun. 12, 1979

[54] APPARATUS FOR EVALUATION OF FITNESS OF A MOTOR VEHICLE OPERATOR TO PERFORMANCE OF A PREDETERMINED MOTOR ABILITY TEST

[75] Inventor: Takeshi Ochiai, Toyota, Japan

[73] Assignee: Toyota Jidosha Kogyo Kabushiki Kaisha, Toyota, Japan

[21] Appl. No.: 814,440

[22] Filed: Jul. 11, 1977

[30] Foreign Application Priority Data

Jul. 9, 1976 [JP] Japan .................................. 51-82327

[51] Int. Cl.² .............................................. B60K 28/00
[52] U.S. Cl. ....................................... 340/576; 180/99
[58] Field of Search ................... 340/279, 576; 180/99; 128/2 N; 35/11, 12 D, 22 R, 11 R, 11 A

[56] References Cited

U.S. PATENT DOCUMENTS

| 3,755,776 | 8/1973 | Kotras | 340/279 |
| 3,824,538 | 7/1974 | Slemp | 340/279 |
| 3,918,176 | 11/1975 | Abernethy et al. | 180/99 |
| 4,004,290 | 1/1977 | Kobayashi et al. | 340/279 |
| 4,058,911 | 11/1977 | Story | 180/99 |

*Primary Examiner*—Glen R. Swann, III

*Attorney, Agent, or Firm*—Koda and Androlia

[57] ABSTRACT

A thyristor circuit and an apparatus using the circuit for the prohibition of operation of a motor vehicle by an intoxicated person may be fabricated by combining an ignition switch with an engine locking and unlocking means, timing means, sensing means and an indication means. The normal ignition circuit of a motor vehicle is interrupted by an engine locking and unlocking means. A timing signal is generated by the timing means by selectively charging a circuit in turn is responsive to the performance of the operator in a motor ability test such as the ability to maintain a predetermined amount of steady pressure on a brake pedal. If the operator is successfully performing the test, the charged node achieves a preselected potential and an indication means produces a first cognizable signal which indicates a successful performance. After the operator has successfully performed the test for a predetermined duration, a second cognitive signal is produced by the indication means which indicates that the operator is qualified to operate the vehicle. The normal ignition circuit is then completed by the engine locking and unlocking means in response to the timing signal. The motor vehicle may then be started in the conventional fashion.

11 Claims, 3 Drawing Figures

APPARATUS FOR EVALUATION OF FITNESS OF A MOTOR VEHICLE OPERATOR TO PERFORMANCE OF A PREDETERMINED MOTOR ABILITY TEST

BACKGROUND OF THE INVENTION

1. Field of Invention

The present invention is a circuit and an apparatus using the circuit for prohibiting the improper operation of a vehicle by a physically unfit operator and specifically concerns an analog circuit for prohibiting the improper operation of a vehicle by such an unfit operator in which a steady control task is imposed on the operator for a designated period of time as a means of evaluating his fitness to operate the vehicle.

2. Description of the Prior Art

The operation of a vehicle, such as an automobile, requires that the vehicle operator be in a mentally and physically stable condition at all times. The ability of a vehicle operator to operate a vehicle is affected by the influence of alcohol, overwork, imperfect health, drugs, and other temporarily disabilitating agents. The operation of a vehicle under such mentally and physically abnormal conditions is extremely dangerous to the person and property of both the operator and the public at large. Devices for determining the unfitness of such operators to operate a vehicle, and for prohibiting the operation of the vehicle involved, has been proposed in the past. In conventional devices of this type, the vehicle operator is given, as a test, appropriate tasks to perform before starting the vehicle into motion. The engine may be started only if the operator shows a sufficient response to the test. Conventional tasks have required the demonstration of an ability to perform simple calculations, tasks which test reflex characteristics or other movement reactions. Among such tasks used for testing, it is known that a steady control task is able to relatively accurately evaluate the fitness of a vehicle operator, and that it is particularly suited for the detection of temporary disability due to the influence of alcohol or other similarly intoxicating drugs. The term "steady control task" refers to a task which requires the continuous maintenance of a designated exertion of a bodily force or position for a predetermined period of time by the vehicle operator, such as, for example, the maintenance of a uniform foot pressure on an operating pedal, such as a brake, clutch, or gas pedal.

In conventional circuits employing a steady control task, evaluation of force to determine whether it is within the acceptable range is extremely complicated and the evaluating circuit typically requires a complex frequency measuring circuit and other such analysis and disposition circuits. This increases the cost of the system, and also increases the number of possible sources of system malfunction. The mandatory characteristics required in a device, which prohibits the improper operation of a vehicle due to temporary operator disability, is consistent and uniform performance, and high reliability. It is clear that the main problem for this type of device is that since its main function is to selectively disable the operation of the vehicle and since the evaluating device must be used in order to start the engine, such a device must have an extraordinarily high degree of reliability. What is needed then is a steady control task apparatus or circuit for prohibiting the improper operation of a vehicle due to temporary disability of the vehicle operator. The device must be characterized by simplicity, low cost and a high degree of reliability.

BRIEF SUMMARY OF THE INVENTION

The present invention is a circuit for prohibiting operation of a vehicle by a person failing to perform a predetermined motor ability test. The present invention comprises an ignition switch, an engine locking and unlocking means including a thyristor, a timing means, a sensing means and an indication means. The ignition switch is coupled to a source of electrical power. The engine locking and unlocking means, including the thyristor, is coupled to the ignition switch and is employed for selectively coupling a starting signal to the vehicle in response to a validity signal applied to the thyristor. The timing means is coupled to the thyristor and generates the validity signal in response to the performance signal. The sensing means is coupled to the timing means and generates the performance signal in response to the performance of the person on the selected motor ability test. Finally, the indication means is coupled to the timing means and generates at least one indicator signal in response to the validity signal. The timing means of the present invention may generate the validity signal according to the success of the person in performing a steady control task for a predetermined time duration.

The method of the present invention is a circuit for conditioning the operation of a motor vehicle upon the performance of the vehicle operator on a motor ability test comprises the steps of sensing the force exerted by the vehicle operator in a steady control task. The duration of time in which the force is continually maintained within a predetermined range is measured. A plurality of cognizable signals indicating that the force is being maintained within the predetermined range and for a predetermined duration is generated. A validity signal used to actuate a thyristor for selectively permitting conventional initiation of the motor vehicle is then generated when the motor ability test is successfully completed.

The method of the present invention includes the case wherein the step of measuring the duration of time includes counting a plurality of clock signals and comparing the number of counted clock signals with a predetermined reference number to generate the validity signal when the counted number and reference number match. The count of clock signals is reinitialized whenever failure to successfully perform the motor ability test occurs.

The present invention also includes the case wherein the steps of measuring the duration of time includes charging a timing means to a predetermined potential. The timing means produces the validity signal if it is continually charged for the predetermined duration. Typically, the timing means includes an active RC network which triggers a thyristor.

The present invention may employ both analog and digital circuitry as described in greater detail in connection with FIGS. 1 and 2.

DETAILED DESCRIPTION OF THE PREFERRED EMBODIMENTS

The present invention is a circuit for prohibiting the improper operation of a vehicle by a temporarily disabled vehicle operator. The circuit contains a sensing means which detects as an electronic on/off signal, a task performed by the vehicle operator in which the operator continuously maintains a designated holding force for a predetermined period of time. A timing means adds, according to the on/off signals of the sensing means, the period of time during which the designated holding force is maintained. The timing means sends out a validity signal when the accumulated time interval reaches a predetermined duration. An engine locking and unlocking means, including a thyristor, closes the normally open conventional ignition circuit to permit starting of the vehicle. Indication means may be included to provide a cognitive feedback to the vehicle operator both as to the status of his performance during the test as well as his ultimate successful or unsuccessful performance.

The present invention is particularly advantageous in that: (1) the holding force employed in the steady control task is detected as an electronic on/off signal; (2) the timing means is a circuit which is activated according to this on/off signal; and (3) the locking and unlocking means is activated to permit operation of the vehicle only when the vehicle operator has satisfactorily performed the steady control task for a predetermined period of time. The present invention and its various embodiments may be better understood by referring to FIG. 1.

Figure 1:
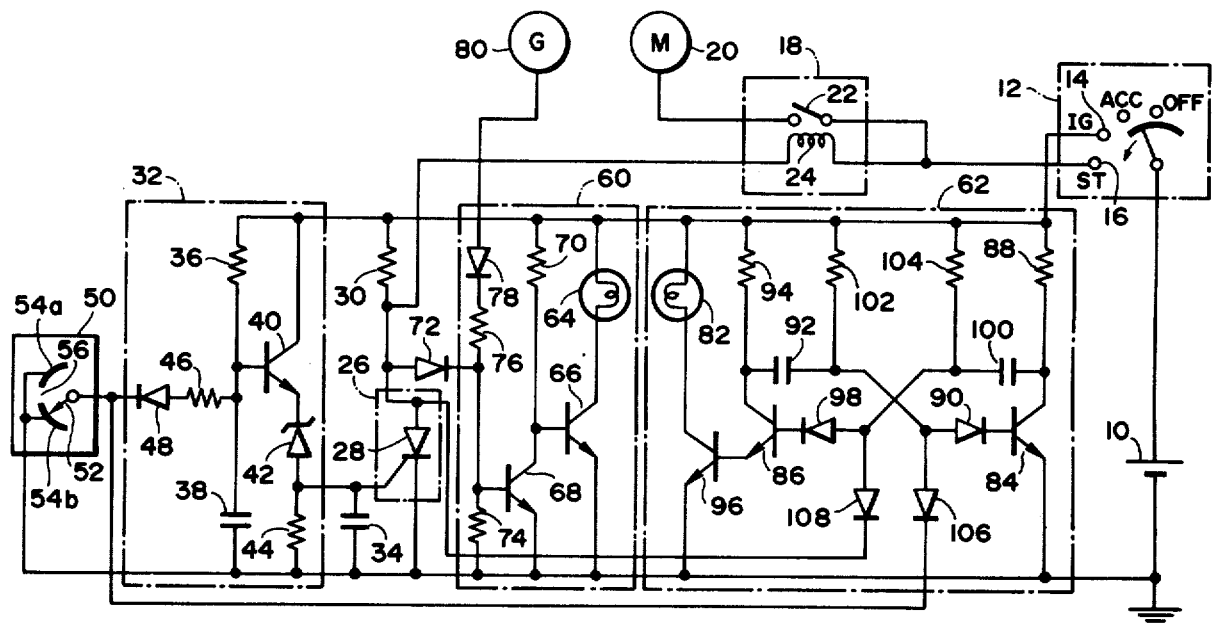
FIG. 1 is a schematic diagram of one embodiment of the present invention showing the use of analog circuitry.

In FIG. 1, voltage is supplied to a conventional starting device for an engine, such as a starter motor or ignition coil, from battery 10 of the vehicle via a conventional ignition switch 12. In the presently illustrated embodiment, the ignition coil circuit (not shown in the figure) is coupled to the ignition terminal 14 of ignition switch 12. Furthermore, starter motor 20 is coupled to starter terminal 16 via an engine locking means 18. Engine locking means 18 may be comprised of a standard relay in which the supply of current to starter motor 20 is interrupted by a normally open relay contact 22. Many other means well known to the art other than electromechanical relays may be used. The example shown should be understood as being shown only for the purposes of illustration. One terminal of relay coil 24 is coupled to starter terminal 16 of ignition switch 12, while the other terminal is grounded through an engine unlocking circuit means 26. Engine unlocking circuit means 26 includes a thyristor 28. Thyristor is a generic title referring to a class of electronic devices consisting typically of four layers of semiconductor material doped with P and N type impurities to form a P-N-P-N structure. Included within this category are silicon-controlled rectifiers, silicon-controlled switches, gate-turn-off switches, various forms of the P-N-P-N diodes, light activated SCR's, and three element static AC switches. For the purposes of the specification and the claims herein, the term "thyristor" is generically used and includes all equivalent devices whether made of semiconductor material or constructed as a standard vacuum tube or other equivalent apparatus. The anode of thyristor 28 is coupled to ignition terminal 14 through a resistor 30 while the cathode is grounded or coupled to a common potential. It is to be further understood that the resistors shown in the present circuit are merely used in the illustration to form a practical device and it is to be understood that further passive and active elements may be added or deleted according to well known principles in order to achieve the desired biases and current distributions as dictated by design choice. Engine unlocking circuit 26 is responsive to a validity signal generated by timing circuit means 32. The validity signal is coupled to the gate terminal of thyristor 28. Accordingly, the receipt of the validity signal causes thyristor 28 to become conductive and engine locking circuit 18 is switched to an unlocked or conductive state. After thyristor 28 has arced or become conductive, engine locking circuit 26 remains in the unlocked or conductive state by virtue of the action of thyristor 28 even after the input of the validity signal is interrupted. In the embodiment illustrated, a noise arresting capacitor 34 is coupled between the gate of thyristor 28 and ground. Many other such modifications may be made to engine unlocking circuit 26 without departing from the scope of the present invention.

Timing circuit 32 forms an adding circuit that adds the operational time of a sensing means, described below, as a voltage value. Timing circuit means 32 as illustrated includes a time-constant circuit comprising a resistor 36 and capacitor 38 coupled in series between ignition terminal 14 and ground. Furthermore, the base of a transistor 40 is coupled to a nodal point between resistor 36 and capacitor 38. The collector of transistor 40 is coupled to ignition terminal 14 and the emitter of transistor 40 is grounded through a zener diode 42 and a resistor 44. The output of timing circuit 32 is coupled from a nodal point between the anode of zener diode 42 and resistor 44 to the gate terminal of thyristor 28 of engine unlocking circuit 26. Accordingly, the potential of the base of transistor 40 varies according to a time-constant established by resistor 36 and capacitor 38. Zener diode 42 becomes conductive when the potential differences between the collector and emitter of transistor 40 drops below a designated value. In other words, as the voltage on the emitter of transistor 40 increases towards the potential of battery 10, a point will be reached, as defined in part by zener diode 42, in which diode 42 will become conductive. This causes a validity signal to be supplied to the gate of thyristor 28. A sensing means circuit 50 is coupled to the base of transistor 40 through a resistor 46 and a diode 48. Sensing circuit 50 includes a movable contact 52 and two fixed contacts 54a and 54b. Movable contact 52 is coupled to the cathode of diode 48 while fixed contacts 54a and 54b are grounded.

Sensing circuit 50 electronically detects the magnitude of the holding force exerted by the vehicle operator in a steady control task. It can be constructed, for example, with a hydraulic pressure switch (not shown in the figures) installed in one of the brake lines of the vehicle. Of course, many other transducers and test points may be employed and the one disclosed herein is for the purposes of clarification and illustration only. This hydraulic pressure switch detects changes in hydraulic pressure caused by the force applied to the brake pedal by the vehicle operator. If the force applied to the brake pedal is maintained at a designated level, the contact terminal of movable contact 52 is held in an "off" position 56 formed by the gap between fixed contacts 54a and 54b. As a result, the output of sensing circuit 50 will be floating or "off" as long as the force applied to the brake pedal is maintained within the designated range. However, if the force fluctuates beyond the range, sensing circuit 50 will send out an "on" signal as a result of movable contact 52 making contact with one of fixed contacts 54a or 54b.

Figure 3:
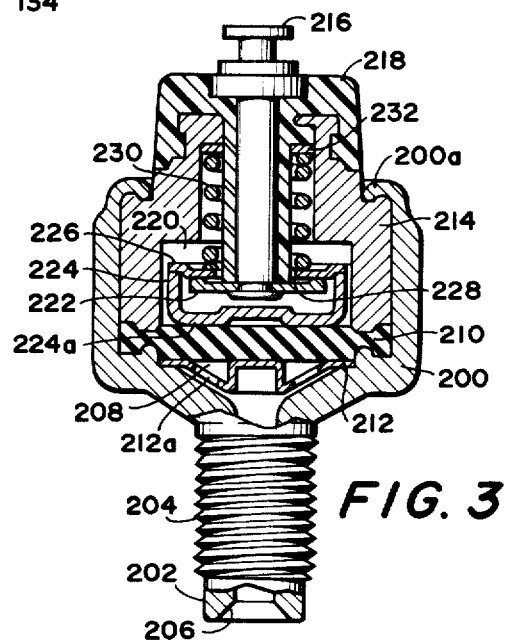
FIG. 3 is a section view of one embodiment of the sensing means of this invention.

One example construction of the sensing circuit 50 is shown in FIG. 3 wherein like reference numerals are applied to like elements or parts.

As shown, a metallic casing 200 forms at the lower end a fluid pressure conducting pipe 202 having male threads 204 therearound and provided with a flare coupling 206 for introduction of the fluid pressure. This fluid pressure or oil-hydraulic pressure conducting pipe 202 is communicated with a fluid pressure chamber 208 defined by a rubber diaphragm 210 which is supported at the lower side by a support plate 212 in chamber 208 while being sandwiched at its circumferential portion between casing 200 and a metallic bushing 214. On metallic bushing 214, is securely supported an electrode 216 through an insulator 218, which electrode 216 extends into an upper chamber 220 defined above diaphragm 210. FIG. 3 shows the position of electrode 216 wherein its lower end is spaced a predetermined distance from diaphragm 210 as no fluid pressure acts in chamber 208.

At the lower end of electrode 216, is supported a radially extending fixed contact element 222 formed integral with electrode 216.

In chamber 220 above diaphragm 210, is provided a movable contact element 224 formed integral with diaphragm 210. This movable contact 224 is in the shape of a bottomed cylinder positioned as surrounding above fixed contact element 222, and is composed of a cylindrical portion with the bottom being secured to diaphragm 210, and a cap-like disc 226 having a central opening 228 through which electrode 216 extends. By means of a spring 230 disposed between a washer 232 and disc 226, both movable contact 224 and diaphragm 210 are biased in the direction to compress fluid pressure chamber 208. Washer 232 is disposed in such manner as to make electrical contact with part of bushing 214.

Diaphragm 210 is normally urged by spring 230 through movable contact 224 in the direction to compress chamber 208, however diaphragm 210 is restrained of its further downward movement beyond the position shown. Support plate 212 forms apertures 212a for communication of fluid pressure into chamber 208. Casing 200 is caulked around its upper circumference 200a thereby to secure bushing 214.

It is arranged that when diaphragm 210 is in its normal position without deformation as shown while fluid pressure in chamber 208 is maintained below a predetermined level, fixed contact element 222 is in contact with the lower side surface of disc plate 226.

This sensing member will operate as follows.

When fluid pressure to be sensed is fed into chamber 208 through conducting pipe 202, fixed contact element 222 will remain in contact with disc plate 226 under the influence of spring 230 biasing diaphragm 210 into the position shown, until the fluid pressure attains a predetermined value. Thus, a circuit is made through electrode 216, fixed contact element 222, disc plate 226, spring 230, washer 232, bushing 214 and casing 200, so that sensing member 50 is in the state of "on".

When the fluid pressure within chamber 208 exceeds the predetermined level, diaphragm 210 is deflected upward against spring 230 to move movable contact element 224 upward, thus disc 226 is moved away from fixed contact element 222 so that sensor now issues an "off" signal.

As the fluid pressure further increases to exceed a further predetermined value, the deflection of diaphragm 210 will increase accordingly so that bottom of cylindrical portion 224a integral with diaphragm 210 will come into contact with electrode 216, thus the output signal from sensor will again become "on".

Hence it is possible to provide "off" signals as long as the fluid pressure is within a predetermined range, and "on" signals when the fluid pressure is otherwise.

The present invention may also include an indication circuit means 60 and 62 which indicate the status of the maintenance of the designated holding force. Indication circuits 60 and 62 are provided in order to inform the vehicle operator whether or not the force he is applying conforms within the predesignated range set by the steady control task. Indication circuit 60 is coupled to engine unlocking circuit 26 and includes a indicating device, such as incandescent lamp 64. Any transducer device capable of producing a cognizable signal may be employed. One terminal of lamp 64 is coupled to ignition terminal 14 while the other terminal of lamp 64 is grounded through the collector and emitter of a transistor 66. The base of transistor 66 is coupled to the collector of transistor 68. The collector of transistor 68 is also coupled to ignition terminal 14 through a resistor 70 and has its emitter grounded. The base of transistor 68 is coupled to anode of thyristor 28 through diode 72. Furthermore, the base of transistor 68 is grounded through resistor 74 and is connected to the output terminal of alternator 80 the vehicle through a resistor 76 and diode 78. Accordingly, lamp 64 of indication circuit 60 is lit when engine unlocking circuit 26 unlocks engine locking circuit 18 and is extinghished when alternator 80 generates voltage after the engine is started. It is to be understood, however, that the anode of diode 78 may be coupled to any other convenient terminal of potential in the vehicle which would indicate that the engine is operating. When the steady control task has been successfully performed, as described below, lamp 64 will light and remain lit until the engine is operating.

The indication circuit means may also include an indication circuit 62 which includes a secondary indicating lamp or incandescent lamp 82. Lamp 82 is caused to flash by an oscillating circuit. In one embodiment, the oscillating circuit may be constructed from an astable multivibrator containing transistors 84 and 86. The collector of transistor 84 is coupled to ignition terminal 14 through a resistor 88 while the emitter is grounded. The base of transistor 84 is coupled to the collector of transistor 86 through a diode 90 and capacitor 92. The collector of transistor 86 is also coupled to ignition terminal 14 through a resistor 94 while the emitter is coupled to the base of a transistor 96. The collector of transistor 96 is coupled to the other terminal of lamp 82 while the emitter is grounded. The base of transistor 86 is coupled to the collector of transistor 84 through a diode 98 and a condenser 100. A resistor 102 is coupled between the anode of diode 90 and ignition terminal 14. Resistor 104 is coupled between the anode of diode 98 and ignition terminal 14. Furthermore, the anode of diode 106 is coupled to the anode of diode 90 while the cathode of diode 106 is coupled to movable contact 52 of sensor means 50. Also, the anode of diode 98 is coupled to the anode of diode 108 while the cathode of diode 108 is coupled to the anode of thyristor 28. As will be explained in detail below, lamp 82 flashes whenever movable contact 52 is in the "off" position and continues to flash until the thyristor becomes conductive.

The operation of the embodiment described in FIG. 1 may be understood as follows. When ignition switch 12 is in an "off" state, thyristor 28 of engine unlocking circuit 26 is in an "off" state. If, at this time, ignition switch 12 is turned to the "start" position, the various component circuits described above are supplied with a voltage from the positive terminal of battery 10 through ignition terminal 14. Since thyristor 28 is in a nonconductive state, transistor 68 of circuit 60 is in an "on" state and which its base potential is maintained by the voltage divided between resistors 30 and 74. Consequently, the potential at the base of transistor 66 is set very near ground potential and transistor 66 is switched "off". Accordingly, lamp 64 is unlit. On the other hand, since the base of transistor 84 is grounded through sensor means 50, and since diode 108, coupled to the base of transistor 86, is coupled to the anode of the presently nonconductive thyristor 28, transistors 86 and 96 are switched "on" and lamp 82 is lit. Of course, the engine cannot be started since thyristor 28 is nonconductive and relay coil 24 of engine locking circuit 18 is nonenergized. Therefore, no current is supplied to starter motor 20.

At this point, the vehicle operator performs the steady control task chosen, such as applying a specified force to the brake pedal. Movable contact 52 of sensor means 50 is moved to an "off" position 56 by the force applied to the pedal by the vehicle operator. This movement causes the output of sensor means 50 to be an "off" signal and switches transistor 84 of circuit 62 such that the potential at its base goes high. Thus, the oscillating circuit included within circuit 62 begins oscillation and lamp 82 begins to flash. The flashing of lamp 82 indicates that the force applied to the pedal by the vehicle operator is at the predetermined level. Accordingly, the vehicle operator must continually maintain the force at this level.

The "off" signal from sensing means 50 is coupled to timing circuit 32. Before the performance of the vehicle operator begins to be tested by the steady control task, capacitor 38 is discharged by timing circuit 32 which includes resistor 46, diode 48 and sensing means 50. However, the switching of sensing means 50 to an "off" state causes this discharge path to be interrupted. A charging current then flows into capacitor 38 from ignition terminal 14 through resistor 36. The voltage produced by this charge is coupled as a performance signal to the gate of thyristor 28 through the threshold circuit formed by transistor 40 and zener diode 42. In other words, if the vehicle operator continues to cause sensing means 50 to send out an "off" for the predetermined period of time, condensor 38 will, during that time, continue to be charged. When the voltage across capacitor 38 exceeds a predetermined value, as set by the breakdown voltage of zener diode 42, the gate of thyristor 28 is supplied with a trigger signal. However, if the force applied by the vehicle operator is unsteady, movable contact 52 of sensing means 50 will make contact with one or both of fixed contacts 54a or 54b. In such a case, a discharge path is formed by resistor 46 and diode 48. The charge accumulated up to that time is rapidly discharged and generation of the performance signal is nullified. Accordingly, since the vehicle operator cannot maintain the force applied to the pedal when he is in an intoxicated or unfit condition to operate a vehicle, he cannot cause the activation of engine unlocking circuit 26. Thus, the energization of coil 24, the unlocking of engine unlocking device 18, cannot be caused by a person unfit to operate the vehicle.

If the force applied by the vehicle operator is maintained at the predetermined levels for the designated period of time, a performance signal is applied to engine unlocking circuit 26 by timing circuit 32. Thyristor 28 then becomes conductive. Thus, relay coil 24 of engine locking circuit 18 is energized by current flowing from battery 10 through starter terminal 16. The relay contact 22 is then switched "on". Accordingly, current is supplied to starter motor 20 from starter terminal 16 and it becomes possible to then start the engine in the conventional manner.

Once thyristor 28 has become conductive, its conductivity is maintained as long as the anode voltage is not interrupted, and as long as no negative gate signal is sent to the gate terminal. Thus, the engine can be started even though the vehicle operator should release the pedal.

Indication circuit 60 provides a cognizable indication of whether or not the operator is fit to operate the vehicle. In other words, when thyristor 28 is switched "on", the potential of the base of transistor 68 is driven very nearly to ground. Accordingly, transistor 68 is switched "off". Transistor 66 then is switched "on" and lamp 64 is lit. When lamp 64 is lit, the vehicle operator is able to determine that his fitness to operate the vehicle is satisfactory. At that time, such additional steps as are necessary may be taken to start the engine in a conventional manner.

Furthermore, the switching "off" of transistors 86 and 96 is caused by the modification of the potential at the base of transistor 86 of indication circuit 62. Thyristor 28 becomes conductive thereby dropping the potential at the base of transistor 86 to very nearly ground. Indicating lamp 82 then ceases to flash.

After the engine has been started, a voltage is generated at the output terminal of alternator 80. This voltage is supplied to the base of transistor 68 of indication circuit 60. Lamp 64 is now extinguished by switching transistor 68 "on" and thus switching transistor 66 "off". Voltage generated by alternator 80 is prevented from flowing over to thyristor 28 by diode 72.

After the evaluation of fitness of the operator is determined and the engine is started as described above, engine locking means 18 is maintained in an unlocked state as long as ignition terminal 14 remains coupled to the positive terminal of battery 10.

In the embodiment of FIG. 1, lamp 64 of indication circuit 60 is typically made to generate a green light while lamp 82 of indication circuit 62 is made to generate a red light, so that the vehicle operator may easily distinguish one from the other.

Figure 2:
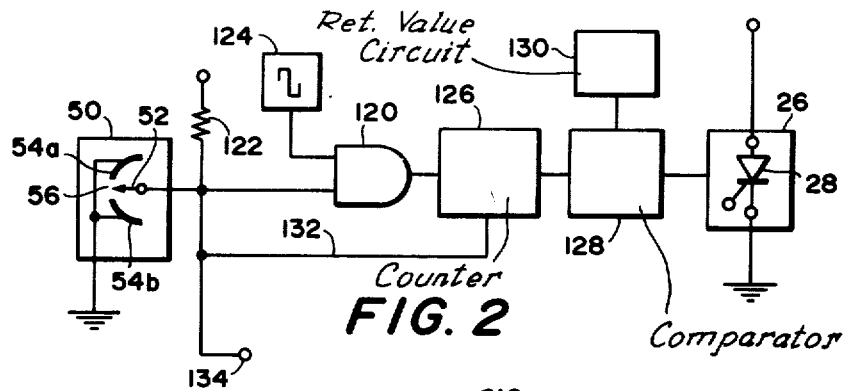
FIG. 2 is a modification of part of the embodiment shown in FIG. 1.

Since it is possible in the embodiment shown and described in connection with FIG. 1 above, to continuously detect the force applied by the vehicle operator and to convert this force into a voltage by utilizing the difference in the charge and discharge characteristics of timing circuit 32, and since it is also possible to unlock the engine locking circuit with the output of the timing circuit, this embodiment possesses the advantage of having an extremely simple circuit construction. In the embodiment shown, timing circuit 32 is indicated by a time-constant circuit formed by a resistor and condenser. However, any other time-constant circuits could also be employed. Furthermore, the threshold circuits formed by transistor 40 and zener diode 42 could also be replaced by any equivalent circuit well known to the art. Also, sensor means 50 need not be a switch which detects the pressure of brake fluid. A switch installed in the brake pedal or clutch pedal or some other type of detection switch suited for a steady control task would also be appropriate. Furthermore, engine locking circuit 18 need not be coupled to the starter motor circuit, but could also be coupled to the ignition coil circuit or any system or subsystem of an engine to prevent its operation. For example, FIG. 2 illustrates another embodiment of the present invention. FIG. 2 illustrates an alternative form of timing means 32 which may be employed in the circuit of FIG. 1.

Movable contact 52 of sensing means 50 is coupled to one input terminal of AND gate 120. This input terminal of AND gate 120 supplied with voltage from the positive terminal of the battery through a resistor 122. When sensing means 50 is "off" AND gate 120 is supplied with an input signal. Furthermore, when sensing means 50 is "on", that is, when movable contact 52 has made contact with one of fixed contacts 54a or 54b, AND gate 120 is grounded, the input signal is interrupted. The other terminal of AND gate 120 is coupled to a pulse generator or clock 124 which generates clock pulses possessing a fixed period for use in counting. Clock 124 contains a well known oscillating circuit and frequency dividing circuit and sends out one pulse every few seconds according to design choice to the input terminal of AND gate 120. The output of AND gate 120 is coupled to a counter 126 which typically is comprised of binary flip-flops in a manner well known to the art. Counter 126 accumulates and counts pulses generated by clock 124 while AND gate 120 is also receiving an input signal from sensing means 50. In other words, counter 126 counts the number of coincidences between clock 124 and sensing means 50.

The contents of counter 126 are compared with a reference value established by a reference value circuit 130. Comparison is accomplished by comparing circuit 128. Establishment of the reference value and comparison of the content of counter 126 may be accomplished by any means well known to the art. Typically, a combination of well known logic gates can perform the desired logical comparison. The output of sensing means 50 is also coupled to the reset terminal of counter 126 through line 132. If movable contact 52 makes contact with one of the fixed contacts, counter 126 receives a reset signal and is reinitialized. The output of comparing circuit 128 produces a performance signal which may then be coupled to the gate terminal of a thyristor 28 in a manner substantially similar to that as shown in FIG. 1 to accomplish the goals of the present invention. It is to be understood that buffer circuitry may be required between the logic output of comparing circuit 128 and the gate terminal of thyristor 28 according to design choices and principles well known to the art.

The operation of the embodiment shown by example in FIG. 2 may be understood as follows. The vehicle operator maintains a uniform holding force. The status of this holding force is confirmed by an indicating circuit substantially similar to that as shown in FIG. 1 coupled to terminal 134. The time which the constant control task is successfully performed is added according to the number of pulses counted by counter 126. When the sum of the added values is equal to the reference value, the output of comparing circuit 128 is coupled to the gate of thyristor 28 and the engine locking means is unlocked. If the vehicle operator is in a unfit condition to operate the vehicle, his holding force will fluctuate thereby causing sensing means 50 to send out an "on" signal. Thus, the contents of counter 126 will be reset in the maintenance time added up to that point nullified. Therefore, it will be impossible to unlock the engine locking circuit.

Although the present invention has been shown and described in connection with the illustrated embodiments, such embodiments were used only for the purposes of illustration and example and it must be understood that each of the elements of the present invention may be combined or replaced by their well known equivalents without departing from the scope of the present invention.

I claim:

1. Apparatus for evaluation of fitness of a motor vehicle operator to perform a predetermined motor ability test, comprising:
   a. sensing means for electrically sensing the exertion of an operating force within a predetermined range by said vehicle operator, said sensing means comprising:
      a pressure switch of the type which turns on when the hydraulic pressure in a hydraulic pressure brake circuit is below a first predetermined hydraulic pressure; turns on when the same exceeds a second predetermined hydraulic pressure; and turns off when the same is between the first and the second predetermined hydraulic pressures;
   b. a judging circuit connected to said sensing means, said circuit being adapted to produce a pass signal when said predetermined operating force has continued for a predetermined period, the result of said fitness test being judged satisfactory:
   c. indicator means connected to said sensing means and judging circuit, which indicator effects display of a first indication when said sensor detects said predetermined operating force and a second indication when the latter has continued for said predetermined period; and
   d. engine locking means connected to said judging circuit, said means being adapted to render the vehicle engine operative responsive to said pass signal.

2. Apparatus according to claim 1, wherein said pressure switch comprises a fixed contact element connected to an electrode and a movable contact element formed integral with a diaphragm which is deformable in response to the fluid pressure to be detected, one of said fixed and moveable contact elements being adapted to come in contact with the other at two different positions spaced apart in the direction the diaphragm deforms.

3. Apparatus according to claim 1, wherein said judging circuit includes:
   a. a condenser connected to said pressure switch and adapted to be charged and discharged, respectively, in response to off and on states of said pressure switch; and
   b. a switching circuit connected to said condenser and adapted to be made "on" and "off" depending on the state of charge of said condenser.

4. Apparatus according to claim 3, further including:
   a holding circuit connected to said switching circuit and adapted to hold an output signal from said switching circuit.

5. Apparatus according to claim 4, wherein said holding circuit is a thyristor.

6. Apparatus according to claim 1, wherein said indicator means includes:
   a. indicating lamp; and
   b. indicating lamp operating circuit, which circuit is adapted to activate said indicating lamp continuously when said sensing means does not detect said predetermined force exerted by the vehicle operator, to flash said indicating lamp when said sensing means continues to detect said predetermined force when exerted by the vehicle operator after having detected said predetermined force, and to turn out said indicating lamp when said predetermined force is maintained for said predetermined period.

7. Apparatus according to claim 1 wherein said indicator means comprises:
   a. indicating lamp; and
   b. an indicating lamp operating circuit connected to said judging circuit and indicating lamp, which operating circuit is adapted to light said indicating lamp when said predetermined operating force has continued for said predetermined period.

8. Apparatus according to claim 1, wherein said engine locking means includes:
   a. a relay contact connected in a serial circuit wherein a starter motor is connected to a power source via a starter switch; and
   b. a relay coil connected to said judging circuit, which coil being adapted to turn on said contact when said judging circuit judges the result of the fitness test satisfactory and turn off when otherwise.

9. Apparatus according to claim 1, wherein said judging circuit includes:
   a. a pulse generator for generating electric pulse signals in a predetermined frequency;
   b. a counter connected to said sensor and pulse generator said counter being adapted to count the pulse signals from said pulse generator while the sensor senses said predetermined operating force; and
   c. a comparator circuit connected to said counter and adapted to generate an output only when the number of countings by said counter reaches a predetermined number.

10. Apparatus for evaluation of fitness of a motor vehicle operator to perform a predetermined motor ability test, comprising:
    a. an pressure switch of the type which turns on when the hydraulic pressure in a hydraulic pressure brake circuit is below a first predetermined hydraulic pressure; turns on when the same exceeds a second predetermined hydraulic pressure; and turns off when the same is between said first and second predetermined pressure;
    b. a condenser having both ends connected to said pressure switch, which condenser is adapted to be charged when said pressure switch turns off;
    c. a power switch adapted to connect a power source across said condenser thereby charging said condenser when said pressure switch turns off;
    d. a first transistor having the base and emitter connected to opposite ends of said condenser, which transistor is adapted to turn on when said condenser is charged to a predetermined level of voltage;
    e. a thyristor having the gate connected to the emitter of said first transistor, which thyristor maintains the "on" state after said first transistor has turned on;
    f. a relay in serial connected to said thyristor, which relay is adapted to turn on when the thryistor turns on;
    g. a starter switch disposed in parallel connection to said power switch;
    h. a starter motor for starting a vehicle engine, said starter motor being connected to said power source via said starter switch and relay;
    i. a multi-vibrator connected to the power source via said power switch and having one transistor and a further transistor whose bases are connected via said thyristor and pressure switch, respectively, to ground;
    j. a red lamp connected to said one transistor, which red lamp is adapted to light when said thyristor turns off and pressure switch turns on, to flash when both of said two elements turn off, and to turn off when said thyristor turns on;
    k. a further transistor having the base connected to said thyristor;
    l. a blue lamp connected to said further transistor, which lamp is adapted to turn on when said thyristor and further transistor turn on; and
    m. an alternator connected to the base of said further transistor and being adapted to generate electricity by rotation of the engine.

11. Apparatus for evaluation of fitness of a motor vehicle operator to perform a predetermined motor ability test, comprising:
    a pressure switch means which generates an "on" signal when a pressure greater or less than a predetermined pressure is applied to said switch and an "off" signal when said predetermined pressure is applied to said switch;
    a clock pulse generator;
    an AND gate having its inputs coupled to said pulse generator and said pressure switch means;
    a counter having a counting input and a reset input, said counting input being coupled to output of said AND gate and said reset input coupled to said pressure switch means such that said counter is reset whenever an "on" signal is generated;
    a reference value circuit for setting a reference value;
    a comparator circuit for comparing an output of said counter and said reference value for generating a pass signal whenever said reference value and said output of said counter are equal;
    a thyristor responsive to said pass signal; and
    an engine disabling means responsive to said thyristor.

* * * * *